United States Patent [19]
Nugent

[11] Patent Number: 5,549,004
[45] Date of Patent: Aug. 27, 1996

[54] HAND HELD TUBE WALL THICKNESS ULTRASONIC MEASUREMENT PROBE AND SYSTEM

[76] Inventor: Michael J. Nugent, 706 Beechwood Dr., Washington Township, N.J. 07675

[21] Appl. No.: 396,013

[22] Filed: Feb. 28, 1995

[51] Int. Cl.⁶ .......................... G01N 29/06; G01N 29/10; G01N 29/26
[52] U.S. Cl. .................. 73/622; 73/624; 73/638; 73/640; 376/249; 376/252
[58] Field of Search ............................. 73/620, 622, 624, 73/625, 627, 628, 637, 638, 640, 641, 644; 376/245, 249, 252

[56] References Cited

U.S. PATENT DOCUMENTS

| | | | |
|---|---|---|---|
| Re. 30,926 | 5/1982 | Ross et al. | 73/638 |
| 3,602,306 | 8/1971 | Peterson et al. | |
| 3,765,228 | 10/1973 | Halsey | |
| 3,910,124 | 10/1975 | Halsey | 73/601 |
| 4,010,636 | 3/1977 | Clark et al. | |
| 4,195,530 | 4/1980 | Ross et al. | 73/638 |
| 4,283,952 | 8/1981 | Newman | 73/579 |
| 4,398,421 | 8/1983 | White | 73/597 |
| 4,625,557 | 12/1986 | Rutherford | 73/635 |
| 4,685,334 | 8/1987 | Latimer | 73/599 |
| 4,890,496 | 1/1990 | Birring et al. | 73/597 |
| 5,243,862 | 9/1993 | Latimer | 73/600 |
| 5,363,701 | 11/1994 | Lee et al. | 73/574 |
| 5,404,755 | 4/1995 | Olson et al. | 73/639 |

Primary Examiner—Hezron E. Williams
Assistant Examiner—Rose M. Finley
Attorney, Agent, or Firm—Brooks Haidt Haffner & Delahunty

[57] ABSTRACT

Corrosion damage to the tubes of power plant boiler waterwalls is detected by a portable hand-held ultrasonic scanner probe equipped with plurality of dual element transducers having concave cylindrically curved surfaces for simultaneously examining arcuate areas of walls of several tubes as the probe is moved along the waterwall. Tube wall thickness and probe location data are processed by a computer for detection, display and recording of places where significant tube damage has occurred.

21 Claims, 5 Drawing Sheets

HAND HELD TUBE WALL THICKNESS ULTRASONIC MEASUREMENT PROBE AND SYSTEM

BACKGROUND OF THE INVENTION

1. Field of the Invention

The invention relates to the maintenance of boilers in electric power generating plants and concerns measurement of boiler tube wall thickness for detection of areas of reduced wall thickness. More particularly, the invention relates to a portable, hand-held tube wall thickness measurement scanning probe for ultrasonic inspection of boiler tubes and to the monitoring and analysis of tube wall thickness measurements.

2. Description of the Related Art

Boiler tube failure is a major problem in fossil-fired electric power generating plants. These boiler tube failures commonly occur as the result of erosion and/or corrosion of the metal at the inner surfaces of boiler tube walls. Many of these tube failures are of boiler tubes which constitute the waterwalls of boilers, i.e., the outer walls of the boiler that enclose the furnace.

A large majority of waterwall tube failures are attributable to the localized effect of hydrogen damage, the root cause of which is believed to be salt in-leakage through deteriorating condensers. Replacement of condensers cannot solve the problem of existing damage in power generating plants, many of which have been in operation for decades. Damaged tubes must be found in order to remove them from service before failures occur.

The condition of the boiler tubes can be tested by the use of conventional ultrasonic thickness gauges to determine whether, and at what locations, significant tube wall thickness reduction has occurred. Such testing allows repair or replacement of damaged boiler tubes before holes form in the tube walls.

The testing of boiler tubes with presently available ultrasonic thickness gauges is a labor-intensive and time-consuming procedure which is carried out, for the most part, during power outages, and is therefore limited to the examination of only a very small portion of the total wall surface area of a boiler. A typical boiler of a mid-size (450 MW) turbine-generator may contain over 50 miles of waterwall tubing. Because of the large amount of tubing to be inspected and possibly replaced, and the limited time that it is economically feasible for a boiler to be out of service, it has not been possible to prevent boiler tube failure by routine inspection of boiler tubes with conventional ultrasonic thickness gauges. Recent attempts to make boiler tube inspection faster and easier include the use of ultrasonic scanning probes that provide wall thickness measurement information to data processing units.

Michael J. Nugent and Shannon J. Hansen, "Automated Boiler Waterwall Tube Inspection for Hydrogen Damage", paper presented to the American Society for Nondestructive Testing (ASNT), Fall Conference, November 1993, describes a semiautomated robotic inspection device for locating areas of hydrogen damage in boiler tubing developed and used by Con Edison Company of New York, Inc. The paper describes a motor-driven crawler employing permanent magnets to attach itself to the furnace wall, and having nine dual-element ultrasonic transducers for simultaneous testing of three parallel tubes.

D. M. Schlader et al., "EPRI Portable EMAT Wall Thickness Measurement System", paper presented to the Electric Power Research Institute (EPRI) 4th Conference on Fossil Plant Inspections, San Antonio, Tex., Jan. 18–20, 1994, describes a boiler tube thickness gauge that employs electromagnetic acoustic transducers that do not use a fluid couplant as required for other kinds of ultrasonic testing. A hand-held probe for testing one tube at a time is described.

SUMMARY OF THE INVENTION

The hand-held ultrasonic tube wall thickness probe of the invention employs three cylindrically curved, dual element transducers to scan the walls of three parallel tubes of a boiler wall as the probe is advanced along the wall surface. The probe also has a wheel in rolling contact with tube wall surface to measure the distance traversed by the probe as the probe is advanced so that thin spots can be logged for subsequent further examination and/or repair or replacement of damaged tubes.

The probe of the invention is a hand-held scanner assembly in which the transducers and the measuring wheel are carried by a base which has contoured rollers and a handle so that the inspecting operator can push the scanner probe assembly over the outer surfaces of the boiler tubes of an array of mutually parallel tubes in the longitudinal direction of the tubes. A flexible conduit is connected to the hand scanner probe assembly to deliver water to serve as the fluid couplant for mechanical transfer of ultrahigh frequency sound between the transducers and the pipe wall being tested. The water is distributed to form a thin couplant layer between the cylindrically curved outer surface of each tube and the opposed concave cylindrically curved surface of the dual-element transducer that lies in spaced, opposed position with respect to the tube.

The transducers are connected by a flexible electrical cable to a portable data processor, e.g., a conventional personal computer, and a display device, which can be placed near the part of the tube wall that is undergoing inspection. Another electrical cable connects a shaft encoder, which can be a quadrature square wave encoder, associated with the probe's measuring wheel, to the data processor for coordinating information relating to the probe location with the wall thickness data provided by the transducers to keep track of the tube wall thickness at equally spaced places as the probe is advanced along the length of the tubes of the boiler wall.

The test results are preferably displayed on a cathode ray tube monitor or liquid crystal display at the local data processing station near the area under inspection. The test data is saved for subsequent analysis, when required.

These and other features, objects and advantages of the invention will be more fully understood when the following detailed description of a preferred embodiment is read in view of the accompanying drawings, in which like reference characters designate like parts throughout.

DETAILED DESCRIPTION OF A PREFERRED EMBODIMENT

Figure 1:
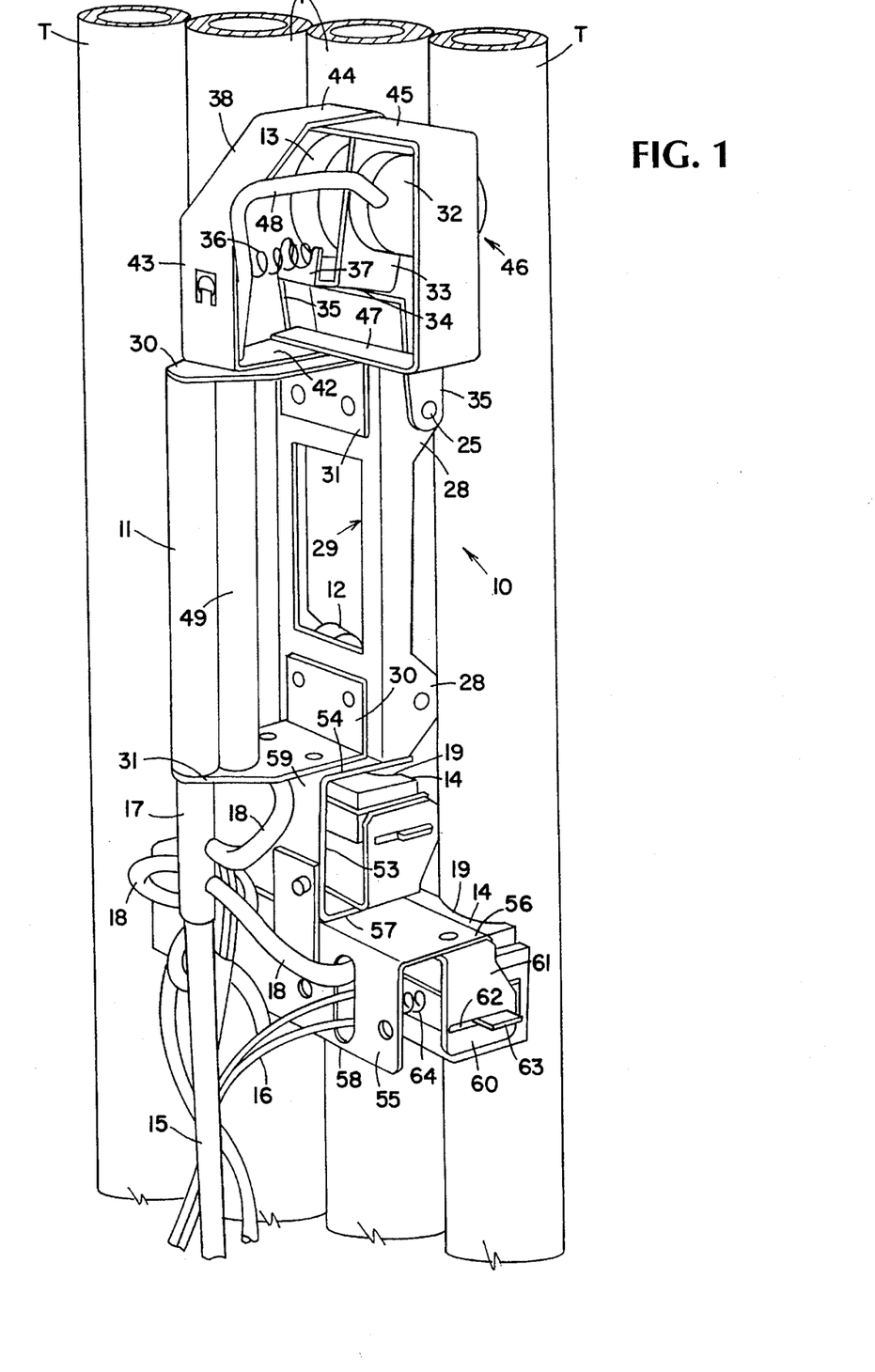
FIG. 1 is an overall view of the hand-held probe assembly of the invention.

The probe assembly generally designated by the reference numeral 10 in FIG. 1 is compact and light enough to be easily used by a worker to inspect a substantial area of a boiler waterwall without operator fatigue. The operator, grasping the handle 11, rolls the probe 10 on its profiled rollers 12 lengthwise along the parallel tubes T which make up the tube wall and the wall thickness measurements are displayed on a monitor screen as scanning progresses.

At its front or leading end (shown at the right in FIG. 1) the probe 10 has a friction wheel 13 for measuring the distance travelled by the probe 10 from the starting point of its traversal of the tubes T. Ultrasonic transducers, generally designated by the reference numeral 14, are mounted to face the outer surfaces of the tubes T near the rear or trailing end of the probe 10 as shown at the left in FIG. 1.

A flexible conduit 15 for delivery of couplant water and electrical cables 16 are shown extending from the rear of the probe 10. The conduit 15 feeds water from a supply of water under pressure (not shown in the drawing) to a cylindrical header or manifold 17 from which three distribution hoses 18 serve to deliver water to the spaces between the cylindrically curved faces 19 of the transducers 15 and the outer surfaces of the tubes T. The cables 16 and water conduit can be of sufficient length, say 10–15 feet (3–5 meters) for an operator to inspect a considerable wall area while the electronic data processing equipment remains in the same nearby location.

To inspect three mutually parallel closely adjacent uniformly sized tubes such as the long metal tubes which make up a boiler wall, the operator, holding the probe handle 11 in one hand, places the probe 10 against the tubes T at a marked and logged position on the boiler wall, with the measuring wheel 13 and the rollers 12 in contact with the outer surfaces of the tube walls in the position illustrated in FIG. 1. Water flow from the conduit 15 to and through the hoses 18 to the tube surfaces is initiated, the electronic components are switched on, and the operator begins advancing the probe 10 along the tubes T (toward the right in the illustration of FIG. 1) always maintaining rolling contact between the measuring wheel 13 and rollers 12 and the tube surfaces as the probe 10 is advanced along the tubes T so that information about the probe location and the tube wall thickness is simultaneously transmitted to the data processing system as the probe 10 is advanced by the operator.

Each of the ultrasonic transducers 14 has a cylindrically curved concave surface 19 which essentially corresponds to the curvature of the tube wall to be examined. The curved transducer face 19 emits sound waves that are directed essentially normal to the tube wall outer surface at the points at which the waves encounter the surface, whereby scanning over a substantial arc of the tube circumference can be carried out. The arc scanned is greater than 60 degrees and preferably about 70 degrees in extent. Prior art probes have employed a plurality of transducers with flat, planar faces to direct sound waves toward the tube surface from different angular positions. For example, three flat surface transducers spaced apart from each other by 30 degrees between adjacent transducers have been employed to examine a tube wall at three points along a 60 degree arc of the tube circumference. However, when the angle of incidence of an ultrasonic sound wave on a surface departs from the ideal 90 degree angle, refraction and mode conversion (shear waves) can be created. The tolerance for deviation from perpendicularity is approximately ±3 degrees. See Robert C. McMaster, *Nondestructive Testing Handbook*, 1959, sections 43–49. The use of a transducer having a curved sound wave emitting surface that matches the curvature of the tubular wall being examined not only provides better results because of perpendicular wave incidence throughout the arcuate region under inspection, but also allows scanning to encompass a wider arcuate band of the tube wall. Dual-element transducers having the geometry required for matching a cylindrical tube wall surface and providing 70 degrees of radial coverage were obtained from Krautkramer Branson Inc. of Lewistown, Pa.

Since the boiler tubes employed in different waterwalls have different diameters, usually from 1 to 4 inches (2.54 to 10.16 cm), the probe must be equipped with transducers selected to match the diameter of the tubes to be examined. A typical boiler tube may have a 1.50 inch (3.81 cm.) outside diameter (O.D.) with a wall thickness of 0.165 inches (0.419 cm.). Only minor modification of the probe according to the invention is needed to accommodate different size transducers for testing of tubes of different sizes. When probe component dimensions are stated in this description, unless otherwise noted, they relate to a probe for testing 1.50" (3.81 cm.) O.D. tubes.

For the testing of 1.5 inch (3.81 cm) tubes, the transducers 14 have a length of 1.20 inches (3.05 cm) and are 0.250 inches (0.635 cm) wide. For 3.00" (7.62 cm) O.D. tubes, transducers 2.40" (6.10 cm) in length would be employed.

Figure 7:
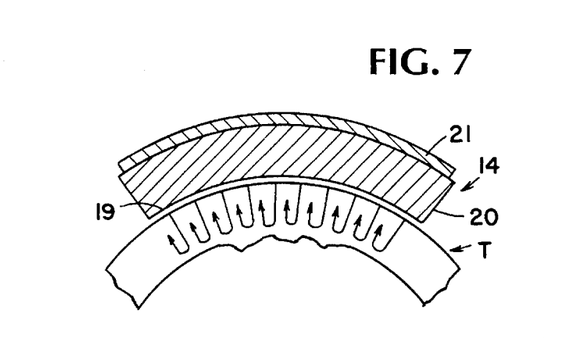
FIG. 7 is a detail view schematically illustrating the reflection of sound waves in a tube wall.
Figure 8:
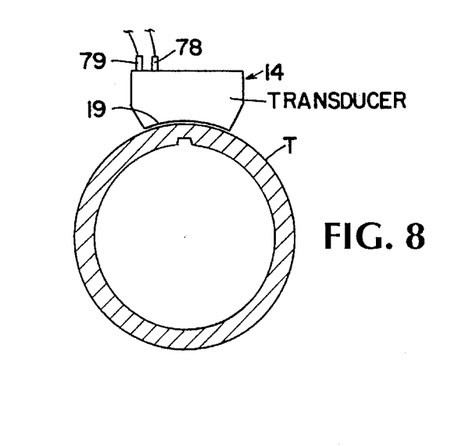
FIG. 8 is a simplified view of a cylindrically curved transducer positioned at an area of reduced tube wall thickness.

The relationship between the transducer 14 and the tube T is illustrated in FIG. 7, wherein the concave cylindrically curved surface 19 of the transducer 14 is seen to be spaced slightly from the correspondingly curved outer surface of the wall of the tube T, so that ultrasound emanating from any point on the concave transducer inner surface 19 will strike the wall of the tube T at an angle of essentially 90 degrees to a plane tangent to the tube surface at the point of incidence. Arrows generally illustrate that the sound is reflected back toward the transducer 14 at the inner surface of the tube T.

The length of time for the sound to pass from the transducer 14 to the inner surface of the tube T and for an echo to return to the transducer 14 is a measure of the thickness of the tube wall. The transducer 14 can have a body 20 of suitable piezoelectric material such as a known ceramic material, and at the rear surface of the transducer, curved concentrically with the inner surface 19, a delay line 21 is schematically shown mounted on the piezoelectric material body 20, as is known in the art of ultrasonic measurement.

The space between the inner transducer surface 19 and the tube 14 is filled with water as a couplant medium for transmitting the sound waves.

The couplant water is supplied from a source of water under pressure (not illustrated) through the flexible conduit 15 shown in FIG. 1 to a water distribution header or manifold 17 shown as a cylindrical pipe section with outlets connected to the ends of three water hoses 18, through which water to serve as the couplant is directed to the surface of the tube T to fill the space between the opposed cylindrical surfaces 19 of the transducer 14 and the tube T.

Figure 3:
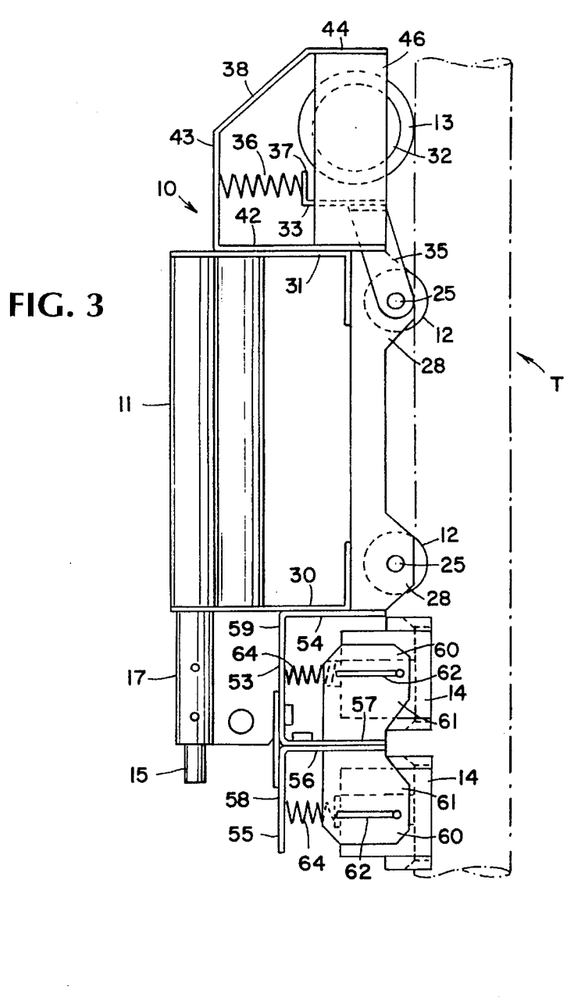
FIG. 3 is a side view of the probe assembly of FIG. 1 in which dashed lines show hidden parts.
Figure 4:
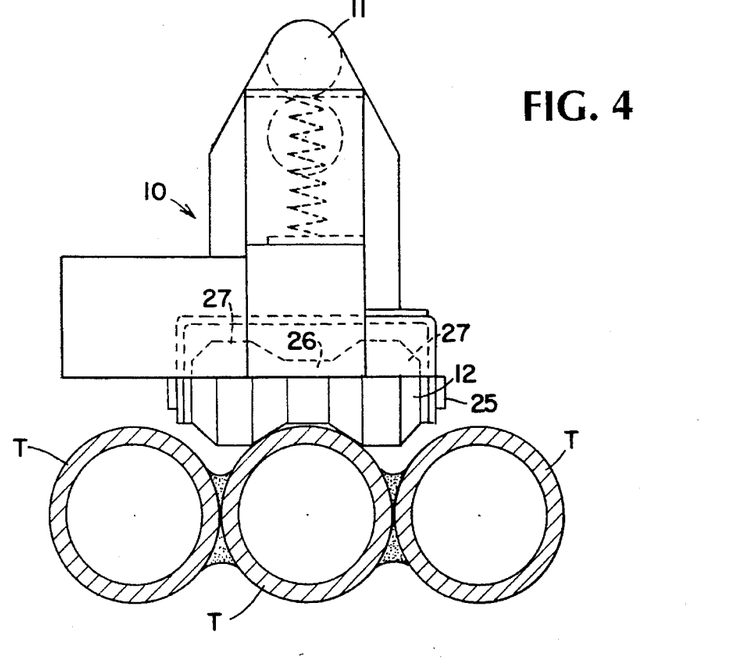
FIG. 4 is a front view of the probe assembly of FIG. 1 in association with a tube wall section, in which dashed lines indicate hidden parts.

FIG. 1 shows the probe assembly 10 for simultaneously testing of three tubes T arranged parallel to each other by moving three of the transducers 14 along the tubes T by rolling the probe 10 on a pair of profiled spaced rollers 12 mounted on axles 25 as shown in FIGS. 3 and 4. FIG. 4 shows the roller 12 to have a central portion 26 of reduced diameter between larger diameter roller portions 27 for guiding the roller 12 along the middle one of three parallel tubes T over which the transducers 14 are carried. The roller profile preferably corresponds generally to the curvature of the tube walls. The ends of the axle 25 extend through spaced parallel legs 28 of the base 29 of the probe 10. At the front and rear ends of the probe base 29 there are mounted upstanding front and rear angle pieces 30, 31 to which opposite ends of the probe handle 11 are secured as shown in FIG. 1.

Figure 2:
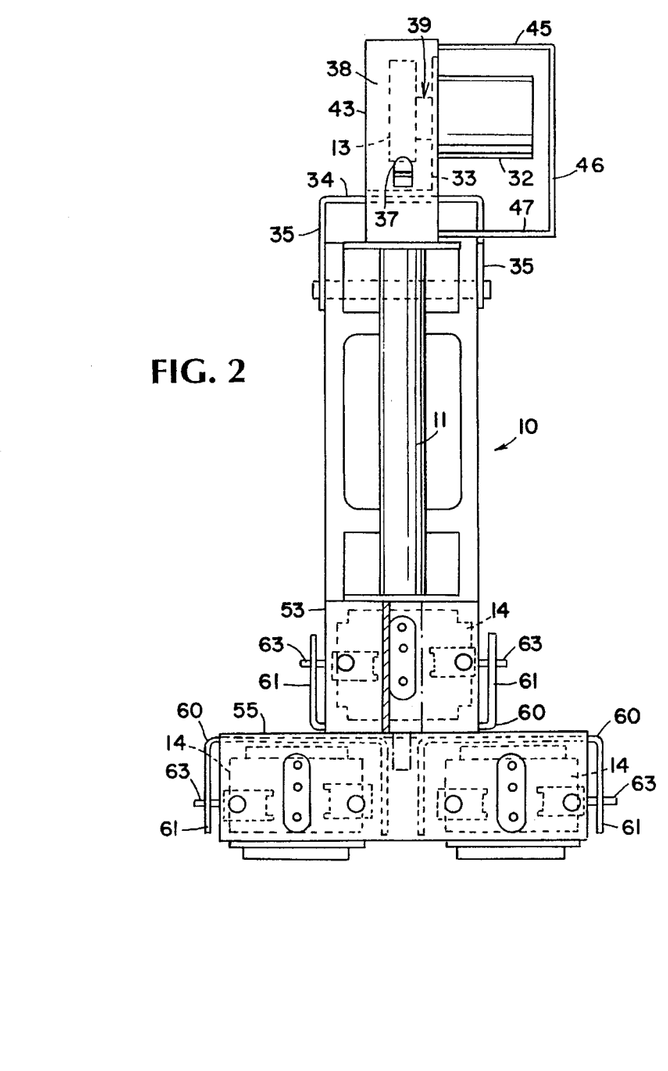
FIG. 2 is a top plan view of the probe assembly of FIG. 1 with hidden parts shown by dashed lines.

The measuring friction wheel 13 that rolls along the outer surface of the middle tube T of the three tubes under examination is carried by a shaft that extends through a bearing 39 fixedly mounted on an arm 33. The shaft, which rotates along with the wheel 13, extends through the bearing 39 to a shaft angle encoder 32, which is preferably a quadrature square wave encoder. Arm 33 is mounted on a generally C-shaped carrier member 34 with a pair of rearwardly extending pivot arms 35. The pivot arms 35 extend toward the rear of the probe 10 on opposite sides thereof and are pivotally connected near outer ends of the front axle 25, all as shown in FIGS. 1, 2 and 3. This pivot arrangement permits the wheel 13 some degree of freedom to move towards and away from the tube axis to accommodate any irregularities in the surface of the tube T over which the wheel 13 travels.

The wheel 13 is maintained in rolling contact with the surface of the tube T by a coiled bias spring 36 under compression. The spring 36 is shown extending between a flange 37 on the arm 33 and an end guard member 38 of the probe 10. The end guard member 38 is secured to the front angle 30 and arches over the wheel 13 and the encoder 32 to protect those elements from damage. The end guard member 38 is shown as having an upstanding leg 42 secured to the front angle 30, a middle portion 43 bent forward at a right angle with respect to the leg 42, and a downward directed front portion 44 positioned ahead of the wheel 13. The coiled spring 36 acts between the end guard middle portion 43 and the flange 37 of the encoder carrying arm 33. The front portion 44 of the end guard member 38 is secured to one leg 45 of a generally C-shaped encoder guard piece 46, the other leg 47 of which is affixed to the front angle 30.

The encoder 32 converts angular displacement, i.e., rotation of the axis or shaft which turns as the wheel 13 rotates, into a pulsed electrical signal for transmission to the data processor where the pulses are counted in order to determine the position of the probe 10. It is presently preferred to use a quadrature square wave encoder that transmits a square wave signal representing rotation of the wheel to the data processor. Suitable quadrature square wave shaft encoders are commercially available. An electrical cable 48 conducts the pulsed electrical signal to the data processor. The cable 48 preferably passes through the interior of a hollow, rigid protective cylindrical member 49 which extends from the front angle 30 to the rear angle 31 lying directly beneath the probe handle 11, and then continues to a connection with the portable computer or other suitable data processor.

The transducer-carrying assembly at the rear end of the probe 10 includes a downwardly opening channel member 53 a front leg 54 of which is secured to the rear angle 31. The channel 53 extends transversely across the rear of the probe base 29. An angle member 55 has one leg 56 secured to the rear leg 57 of the channel 53. The other leg 58 of the angle 55 lies parallel with the web 59 of the channel 53. See FIGS. 1 and 3. Two of the transducers 14 are carried by the angle 55 as shown in FIG. 2 and a central transducer 14 is mounted within the channel 53.

Each of the transducers 14 is allowed some movement toward and away from the tube T which the transducer 14 faces. For this purpose, generally C-shaped guides 60 embrace the transducers 14. Each guide 60 has-a pair of legs 61 spaced apart by a distance slightly greater than the length of the transducers 14. Slots 62 in the legs 61 extend in a plane perpendicular to the axes of the tubes T to permit sliding movement of flat tabs 63 at the ends of the transducers 14. Coiled springs 64 mounted between the outer transducers 14 and the leg 58 of angle 55 and between the middle transducer 14 and the web 59 of the channel 53 urge the transducers toward the tubes T.

Figure 5:
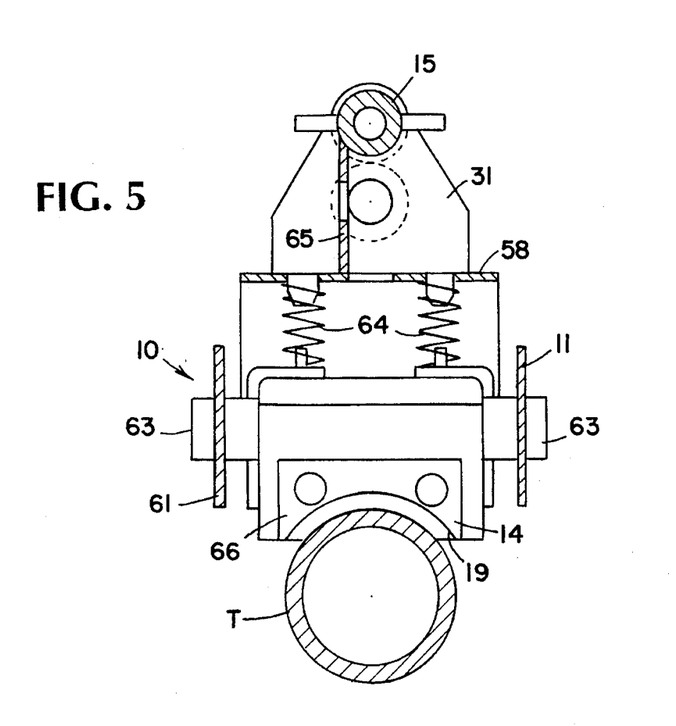
FIG. 5 is a transverse sectional view taken through the probe assembly at the location of a middle transducer of the three transducers and looking toward the front of the probe assembly.

FIG. 5 shows an upstanding flat reinforcement member 65 extending longitudinally and securing the manifold 15 in place, and also shows a wear plate 66 with an arcuate cut-out which is preferably mounted along the side face of each transducer 14 to protect the transducer.

Figure 6:
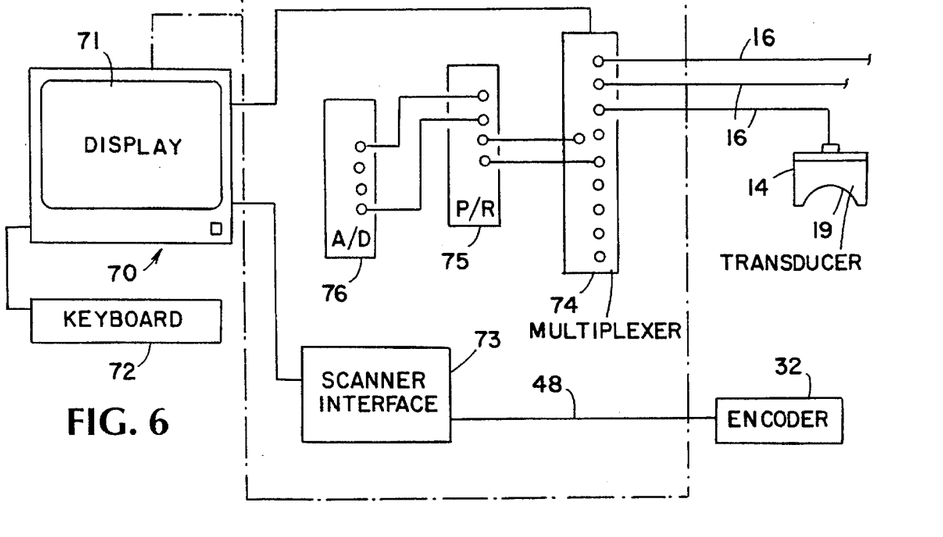
FIG. 6 is a diagrammatic view of the electrical connections of the ultrasonic measurement probe system of the invention.

The diagram of FIG. 6 shows the signal processing arrangement preferably employed with the probe 10 of the invention. A data processing device, which can be a general purpose computer, and is preferably a commercially available personal computer, is designated by reference numeral 70. The computer is equipped with a display screen 71 such as a flat panel liquid crystal display or a CRT display and is also provided with a keyboard 72. A scanner interface board (SIF) 73 which can include an amplifier, is shown connected between the computer 70 and the encoder 32 by cable 48.

Coaxial cables 16 connect the transducers 14 (one of which is shown in FIG. 6) to a multiplexer 74, which is in turn connected to a pulser/receiver (P/R) 75. An analog to digital converter (A/D) 76 is connected to the P/R 75 for digitizing the analog signal from the transducer 14. In the hardware actually used in accordance with the invention, the electronic components 74, 75 and 76 are boards within the same console that houses the central processor of the computer 70.

In the presently preferred system according to the invention, the computer 70 has a 486 processor, 4 megabytes of random access memory, a 240 megabyte hard drive, a 3.5" disk drive and 4 ISA expansion slots.

Infometrics, Inc. TestPro software suitable for use with the Panametrics, Inc. EPOCH II digital ultrasonic flaw detector and the USD10 digital flaw detector manufactured by Krautkramer-Branson can be employed in conjunction with the three-transducer probe of the present invention, provided a suitable six channel multiplexer is employed to accommodate the three dual-element transducer and the program is appropriately adapted. The Infometrics, Inc. TestPro system also includes A/D and P/R boards. A 275 watt power supply is adequate.

When tubes T are being scanned, the probe 10 is advanced along the tubes T at a speed of about 10 to 12 feet (3 to 4 meters) per minute. As the probe 10 moves along, the signal from each transducer 14 is sampled at locations spaced apart by a distance along the tube length of 0.050 inches (0.127 cm). This sampling rate is within the data acquisition limitations of the computer employed. The information thus obtained represents the tube wall thickness at each point. By taking measurements at positions spaced apart by 0.050 inches (0.127 cm), pits in the pipe wall having diameters of 0.250 inches (0.635 cm) are reliably detected.

Figure 9:
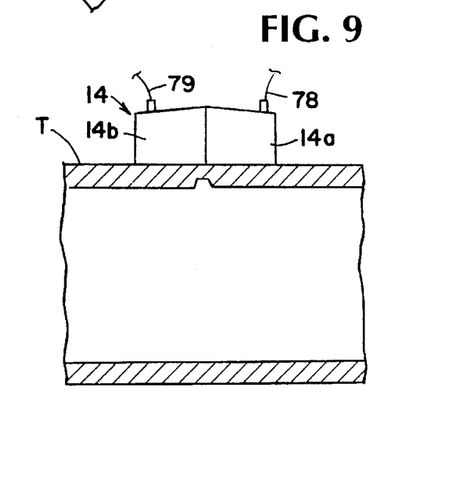
FIG. 9 is a simplified view of a dual-element transducer positioned at an area of reduced tube wall thickness.
Figure 10:
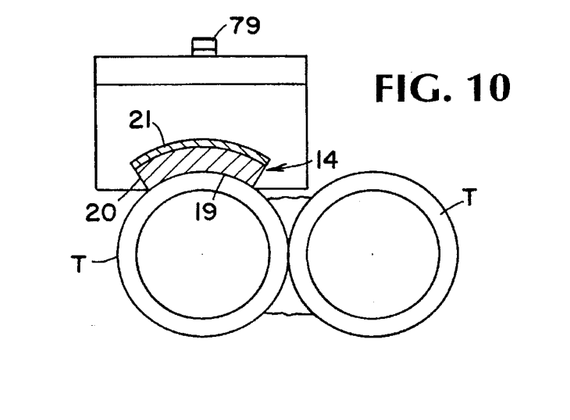
FIG. 10 is a simplified illustration showing the relationship of a transducer of the probe assembly of the invention with two adjacent tube sections under inspection.
Figure 11:
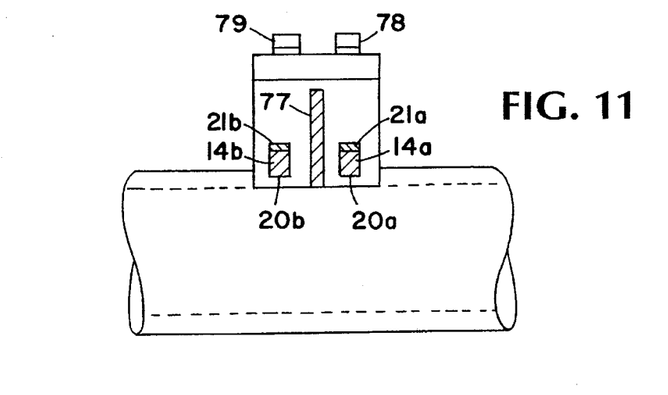
FIG. 11 is a simplified illustration of the relationship of a dual-element transducer of the probe of the invention with a tube under inspection.

Each dual element transducer 14 consists of two transducers, designated as 14a and 14b in the simplified illustrations of FIGS. 9 and 11. The transducer 14a acts as a transmitter of longitudinal sound waves and the transducer 14b serves as a receiver for reflected waves. The piezoelectric material body 20a and its delay line 21a comprising the transducer element 14a are mounted alongside the piezoelectric body 20b and the respective delay line 21b which constitute the transducer 14b. An acoustic barrier 77 separates the elements 14a and 14b, as shown in FIG. 11, so that the receiver element 14b can start detecting echoes before the transmitter element ends transmission.

Most ultrasonic testing is done at frequencies between 1 and 25 MHz. The frequency presently preferred for testing in accordance with the present invention is 5 MHz. A pulsed electrical signal at this frequency is fed to transducer element 14a through the electric conductor 78. The electrical energy carried by the pulse is converted by the piezoelectric body 20a of the transmitting element 14a into a mechanical vibration which passes through the thin film of water covering the surface of the tube T and through the metal wall of the tube until the vibration meets and is reflected off the inner wall surface of the tube 10 to return as an echo to the receiver body 20b of the transducer element 14b, which converts the mechanical vibration to an electrical pulse that exits the receiver element 14b through the electrical conductor 79.

This returning electrical signal is amplified and is converted to a square wave (digitized) by the A/D converter 76. The time of arrival and amplitude of the digitized signal is measured and used to compute the wall thickness by means of the computer software. The measurements are displayed and plotted on the CRT display screen 71.

Meanwhile, the wheel 13 is measuring the portion to which the probe 10 has moved along the tube 10 and the encoder 32 produces a square wave signal which shows when the probe 10 has advanced by successive 0.050 inch (0.127 cm) increments along the tube length. This information is also fed (via the cable 48 and scanner interface 73 to the computer 70 where a record of the signal received at each of the closely spaced locations along the wall of the tube T is produced.

Since each transducer 14 has a curved shape extending over a 70 degree arc, the data on tube wall thickness represent measurements along arcs cut through the tube every 0.050 inches (0.127 cm) along the length of each of the three tubes T undergoing scanning simultaneously. Large portions of the waterwall of boiler can accordingly be economically scanned within a reasonable time, for example the 8 to 12 hour duration of an outage planned by a power generating utility to occur over a weekend period of low electric power demand.

Figure 12:
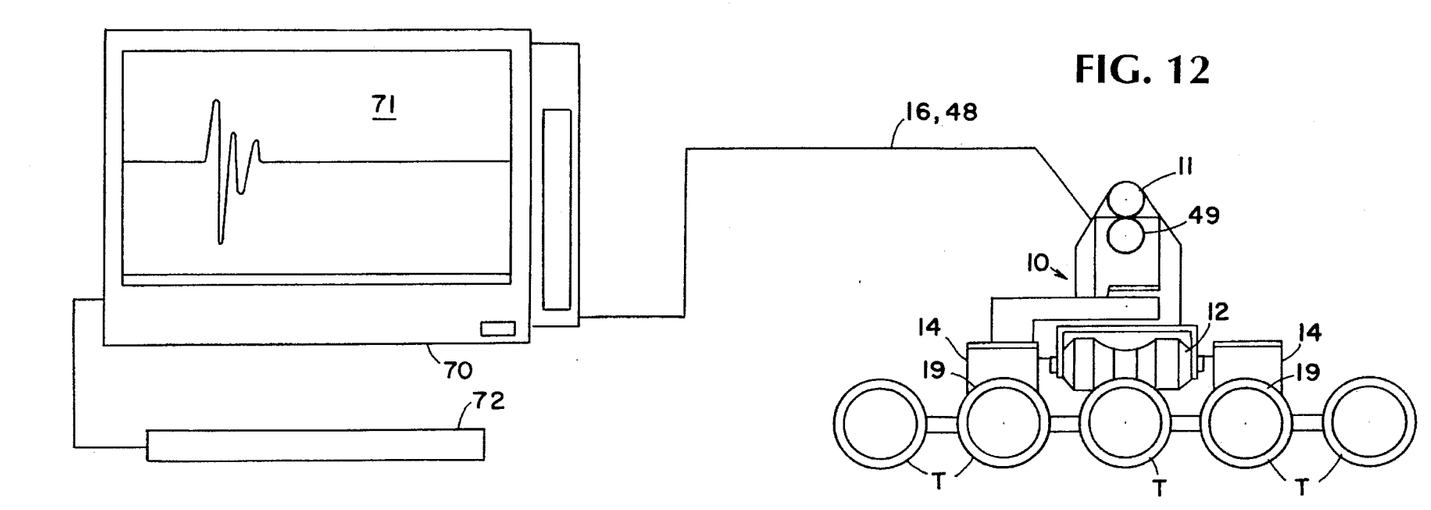
FIG. 12 is a simplified illustration of a probe according to the invention and a CRT monitor.

FIG. 12 schematically shows the waterwall inspection procedure. With the boiler shut down, the outer tube surfaces in the waterwall, or in the region of the wall to be inspected, are cleaned so that the tube surfaces are generally smooth. Five tubes are shown in section in the drawing as representing a boiler waterwall. The operator using the probe 10 places and holds the probe 10, with the rollers 12 embracing a tube 10 at some chosen starting point. Water flow to the probe 10 through the conduit 15 is turned on, and the water forms a thin layer between the faces 19 of the transducers 14 and the surfaces of the tubes T.

The power is switched on to operate the computer 70, display 71 and associated circuitry. A second testing operator, at the keyboard 72, initiates the testing procedure by entering the appropriate commands. A display on the screen 71 shows that testing is ready to begin, and the operator handling the probe 10 moves the probe 10 along the tubes T at a steady rate of advancement as a display on the screen 71 shows a trace representing tube wall thickness. The wall thickness data is stored on a suitable recording medium such as a disk for later analysis, if desired. When the operator holding the probe 10 reaches a convenient place to interrupt testing for repositioning of the probe 10, the operator at the keyboard 72 enters another command. The probe 10 is moved to another spot, which might be three tube-widths away from, and alongside the starting point, and scanning is again begun. In this way, two operators can scan a substantial wall area in the course of a working shift.

It has been found desirable to note only spots where the tube wall thickness is reduced by 20% or more from the original wall thickness. An alarm gate can be set to signal and make a record of wall thickness signals at points where wall thickness measurements are less than 80% of a preset value, say at 0.148 inches (0.376 cm). The spots where such wall thinning has occurred can be physically marked by application of spray paint or other visible marking on the walls of the damaged tubes. These tubes can then be removed, and sections thereof, or entire tubes, can be replaced. This marking can be done at the time wall damage is detected, or at a later time in accordance with computer generated records.

The probe 10 of the invention has been described as embodied by a probe 10 for simultaneous examination of three 1.5 inch (3.81 cm) tubes T, but if larger tubes were to be inspected, the probe could have two transducers 14 instead of the three shown. For the three transducer probe 10 described in detail, the dimensions are: 12.0 inches (30.5 cm) length; 6.0 inches (15.2 cm) width; 4.0 inches (10.2 cm) height. The probe 10, of stainless steel construction, weighs about 3 pounds (1.36 kilograms). A probe of this size and weight can be conveniently carried in one hand and used without operator fatigue. The combination of fifteen foot (4.57 meter) 0.50 inch (1.27 cm) diameter flexible water conduit 15 and electrical coaxial cables 16 (with cable shields) weighs about 2 pounds (0.9 kilograms).

Variations and modifications of the particularly preferred embodiment of the apparatus shown and described, as well as applications thereof will suggest themselves to those acquainted with non-destructive testing technology and such adaptations are considered to be within the spirit and scope of the invention.

What is claimed is:

1. A portable hand-held scanner having a plurality of transducers for converting electrical signals to ultrasonic pulses, transmitting the ultrasonic pulses, receiving return reflected ultrasonic pulses and converting the reflected pulses back into electrical signals for simultaneous examination of the thickness of walls of a plurality of adjacent parallel cylindrical tubes to locate areas of reduced tube wall thickness connected to means for measuring time intervals between transmission of the ultrasonic pulses and receipt of corresponding return ultrasonic pulses reflected off the inner wall surface of each tube wall to measure tube wall thickness as a probe moves parallel to the axes of the parallel cylindrical tubes, which comprises a movable probe body carrying said plurality of transducers each of said transducers having a concave cylindrically curved surface corresponding to and in uniformly spaced, opposed relation to an outer surface of one tube of the plurality of adjacent tubes under examination for transmitting the ultrasonic pulses through an arcuate portion of the wall of the tube to produce the return pulses by reflection off the inner wall surface, means carried by the probe body for measuring the distance the probe has moved; and means for associating corresponding time intervals and distance measurements for each tube of the plurality of tubes.

2. The scanner of claim 1 wherein each transducer is a dual-element transducer having a transmitter and a receiver separated by an acoustic barrier.

3. The scanner of claim 1 wherein the curved surface of each transducer extends through an arc greater than 60 degrees.

4. The scanner of claim 1 wherein the curved surface of each transducer extends through an arc of about 70 degrees.

5. The scanner of claim 1 wherein the distance measuring means comprises a shaft encoder mounted on a shaft of a wheel of the probe in rolling contact with the surface of a tube under examination.

6. The scanner of claim 1 wherein the distance measuring means comprises a quadrature square wave encoder mounted on a shaft of a wheel of the probe in rolling contact with the surface of a tube under examination.

7. The scanner of claim 1 wherein the distance measuring means comprises a shaft encoder mounted on a shaft of a wheel of the probe in rolling contact with the surface of a tube under examination and including spring means for allowing relative movement of the wheel with respect to the probe body.

8. The scanner of claim 1 wherein the probe body has at least one roller for rolling the probe along a tube.

9. The scanner of claim 1 wherein the probe body has two rollers for rolling the probe along a tube.

10. The scanner of claim 1 wherein the probe body has two rollers for rolling the probe along the tubes, said rollers having profiled surfaces for guiding the probe to move along a line parallel to the axis of a tube under examination.

11. The scanner of claim 1 wherein the probe carries two transducers mounted side by side for simultaneous inspection of two parallel tubes.

12. The scanner of claim 1 wherein the probe carries three transducers for simultaneous inspection of three parallel tubes.

13. The scanner of claim 1 wherein housings of the transducers are mounted for limited motion toward and away from the tubes and including spring means for urging the transducers toward the tubes.

14. Apparatus for simultaneous examination of the thickness of walls of a plurality of adjacent parallel tubes to locate areas of reduced wall thickness comprising means for measuring time intervals between transmission of ultrasonic pulses by a plurality of transducers and receipt by said transducers of return pulses reflected off the inner wall surface of each tube wall, and including a hand-held probe having rollers mounted to guide the probe along the length of one of the tubes, said plurality of transducers being mounted in the probe, each transducer having a cylindrically curved face corresponding to and in uniformly spaced, opposed relation to an outer surface of a tube under examination for transmitting said ultrasonic pulses through an arcuate portion of the wall of the tube under examination and for receiving reflected return pulses and converting the return pulses into electrical signals, means carried by the probe for measuring the distance the probe has moved along the length of the tubes, means for conducting electrical signals representative of the tube wall thickness and distance measurements to signal processing means remote from the probe and means for associating and analyzing corresponding time interval and distance measurement signals for locating areas of reduced tube wall thickness.

15. The apparatus of claim 14 wherein the distance measuring means includes a wheel mounted in the probe for rolling contact with a tube wall and a shaft encoder coupled with said wheel for providing the signal representation of the distance measurement.

16. The apparatus of claim 15 wherein the shaft encoder is a quadrature square wave encoder.

17. The apparatus of claim 14 wherein the signal processing means includes an analog to digital converter for digitizing the signal representation of wall thickness.

18. The apparatus of claim 14 and including a conduit for supplying water to the probe to act as an acoustic couplant between the transducers and the tube walls.

19. The apparatus of claim 14 wherein there are three transducers and wherein the means for conducting the electrical signals representative of tube wall thickness includes a multiplexer.

20. The apparatus of claim 14 and including a monitor for visual display of wall thickness and time interval measurement information.

21. The apparatus of claim 14 wherein each of said transducers is a dual element transducer comprising a transmitter and a receiver separated by an acoustic barrier.

* * * * *